US00PP26420P2

(12) United States Plant Patent
Jamieson

(10) Patent No.: US PP26,420 P2
(45) Date of Patent: Feb. 16, 2016

(54) *AGAPANTHUS* PLANT NAMED 'BLUE BAYOU'

(50) Latin Name: *Agapanthus praecox*
Varietal Denomination: Blue Bayou

(71) Applicant: Richard Jamieson, Kirstenhof (ZA)

(72) Inventor: Richard Jamieson, Kirstenhof (ZA)

(73) Assignee: THE PINK GERANIUM NURSERY, Elsenburg (ZA)

( * ) Notice: Subject to any disclaimer, the term of this patent is extended or adjusted under 35 U.S.C. 154(b) by 10 days.

(21) Appl. No.: 13/999,106

(22) Filed: Jan. 13, 2014

(51) Int. Cl.
*A01H 5/02* (2006.01)

(52) U.S. Cl.
USPC ..... Plt./398

(58) Field of Classification Search
USPC ..... Plt./398
CPC ..... A01H 5/02
See application file for complete search history.

(56) References Cited

PUBLICATIONS http://www.plantsinstock.co.za/plant_facts$_{13}$ 8506_agapanthus-blue-less-than-100cm 3 pages, 2010.*

* cited by examiner

*Primary Examiner* — Kent L Bell
(74) *Attorney, Agent, or Firm* — Penny J. Aguirre

(57) ABSTRACT

A new cultivar of *Agapanthus* named 'Blue Bayou', that is characterized by its robust plant habit, its short, stiff flowering stems, its large flowering heads of deep magenta blue flowers, and its extended bloom period.

2 Drawing Sheets

Botanical classification: *Agapanthus praecox*.
Varietal denomination: 'Blue Bayou'.

BACKGROUND OF THE INVENTION

The present invention relates to a new and distinct cultivar of *Agapanthus praecox* and will be referred to hereafter by its cultivar name, 'Blue Bayou'. 'Blue Bayou' represents a new perennial herb grown for landscape use.

The new *Agapanthus* originated as the result of an on going breeding program in Cape Town, Republic of South Africa. The goal of the breeding program was to produce a cultivar of *Agapanthus* with a robust plant habit, a large flowering head and an extended bloom period.

'Blue Bayou' originated as a seedling that arose from seed planted from open pollination of an unnamed plant of *Agapanthus praecox* from the Inventor's breeding program in 2002. The male parent is unknown. The new *Agapanthus* was selected as a single unique plant in December of 2004.

Asexual propagation of the new cultivar was first accomplished by in vitro propagation under the direction of the Inventor in December of 2005 in Cape Town, Republic of South Africa. Asexual propagation by division and tissue culture has determined that the characteristics of this cultivar are stable and are reproduced true to type in successive generations.

SUMMARY OF THE INVENTION

The following traits have been repeatedly observed and represent the characteristics of the new cultivar. The characteristics in combination distinguish 'Blue Bayou' as a distinct cultivar of *Agapanthus*.

1. 'Blue Bayou' exhibits a robust plant habit.
2. 'Blue Bayou' exhibits short, stiff flowering stems.

3. 'Blue Bayou' exhibits large flowering heads of deep magenta blue flowers.
4. 'Blue Bayou' exhibits an extended bloom period.

The female parent differs from 'Blue Bayou' in having slightly larger flowering heads, longer stems, and a lighter flower color. 'Blue Bayou' can be compared to the cultivars 'Peter Pan' (not patented) and 'Snowball' (not patented). 'Peter Pan' is similar to 'Blue Bayou' in being evergreen and in having blue flowers, but 'Peter Pan' differs from 'Blue Bayou' in having smaller flower heads of lighter blue flowers and in having less robust flower stems. 'Snowball' is similar to 'Blue Bayou' in being evergreen. 'Snowball' differs from 'Blue Bayou' in having smaller flower heads of white flowers, shorter flowering stems, and leaves that are smaller and darker green in color.

BRIEF DESCRIPTION OF THE DRAWINGS

The accompanying colored photographs illustrate the overall appearance and distinct characteristics of the new *Agapanthus*. The photographs were taken of a three year-old plant of 'Blue Bayou' as field grown outdoors in Cape Town, Republic of South Africa.

The photograph in FIG. 1 provides a close-up view of an inflorescence of 'Blue Bayou'.

Figure 1:
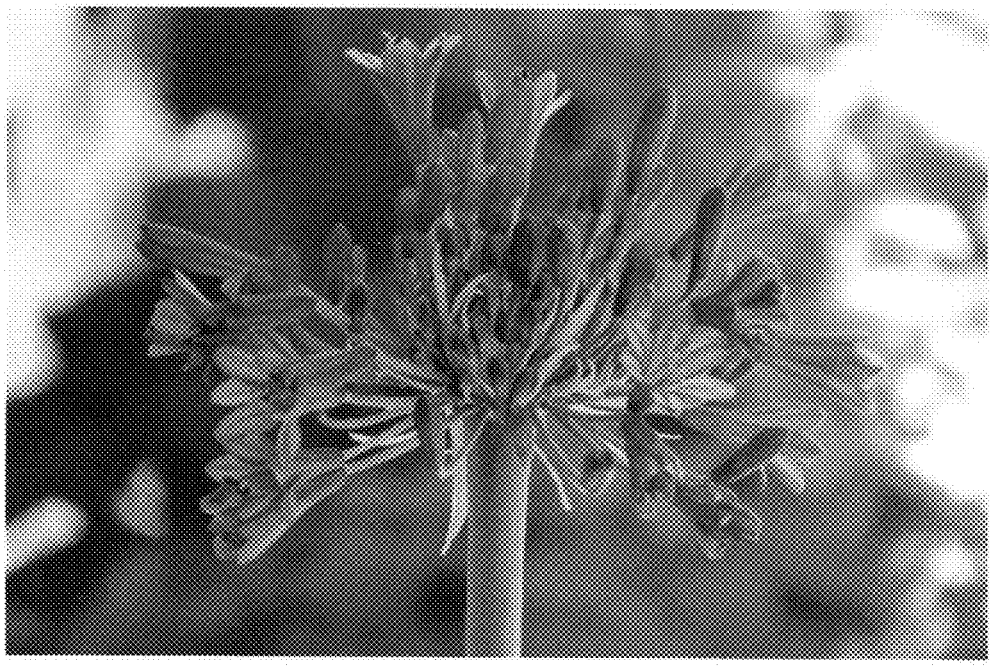
Figure 2:
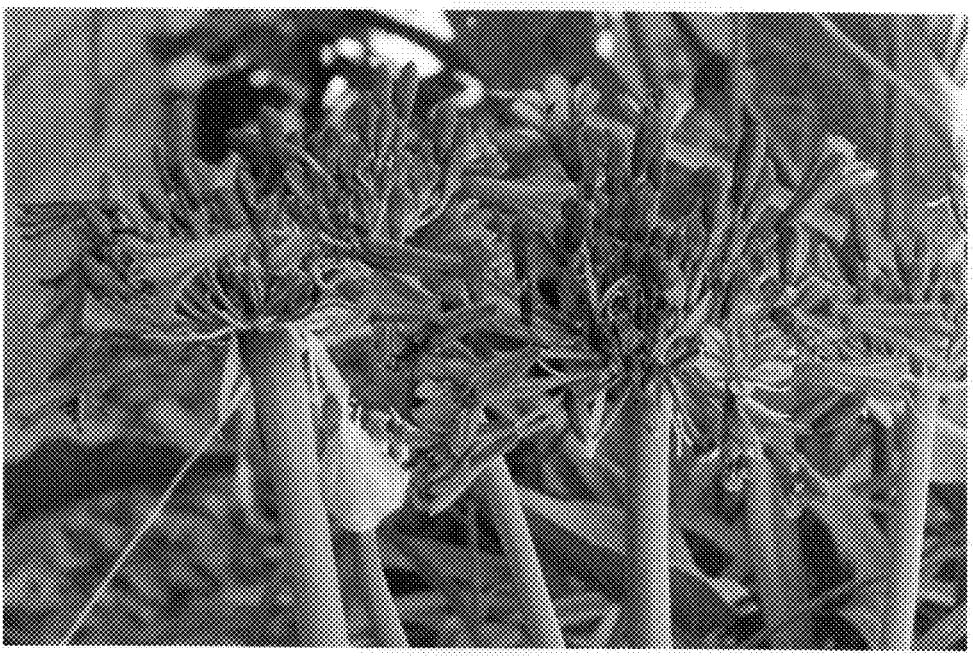

The photograph in FIG. 2 provides a close-up view of the flowers of 'Blue Bayou'.

The colors in the photographs are as close as possible with the photographic and printing technology utilized and color values cited in the detailed botanical description accurately describe the colors of the new *Agapanthus*.

DETAILED BOTANICAL DESCRIPTION

The general observations and descriptions describe plants about two year-old in age as grown outdoors under field conditions in Cape Town, Republic of South Africa. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming period*.—Blooms for 8 to 10 weeks in mid summer in Cape Town, Republic of South Africa.

*Plant type*.—Evergreen perennial herb.

*Plant habit*.—Upright with cascading foliage, and robust short flowering stems.

*Height and spread*.—Reaches a height of about 45 cm in bloom and a spread of about 37 cm.

*Cold hardiness*.—At least to U.S.D.A. Zone 8.

*Diseases and pests*.—No susceptibility or resistance to diseases or pests has been observed.

*Root description*.—Fleshy main roots and fibrous secondary roots.

*Propagation*.—Tissue culture and division.

*Growth rate*.—Moderate.

Foliage description:

*Leaf shape*.—Linear.

*Leaf division*.—Simple.

*Leaf base*.—Cuneate.

*Leaf arrangement*.—2-ranked, in rosette.

*Leaf apex*.—Acute.

*Leaf aspect*.—Emerging leaves erect, then cascade.

*Leaf venation*.—Parallel, color matches leaf coloration.

*Leaf margins*.—Entire.

*Leaf size*.—Average of 22 cm in length and 2.5 cm in width.

*Leaf surface*.—Glabrous, slightly glossy.

*Leaf substance*.—Thick and leathery, moderate to high durability to stress.

*Leaf number*.—Average of 7 per rosette.

*Leaf color*.—Young leaves, upper surface; Yellow-Green 145A, young leaves, lower surface; Yellow-Green 145A mature leaves, upper surface; Yellow-Green 146C and White 157D near base, mature leaves, lower surface; Yellow-Green 145B and White 157D near base.

*Leaf attachment*.—Sessile to crown.

Flower description:

*Inflorescence type*.—Simple umbel.

*Flower fragrance*.—None.

*Flower type*.—Campanulate.

*Flower number*.—An average of about 70 flowers per umbel, one umbel per peduncle and one peduncle per rosette.

*Inflorescence size*.—Average of 8 cm in depth and 15 cm in diameter.

*Flower size*.—About 3.5 cm in depth and 1 cm in width.

*Lastingness of inflorescence*.—About 35 days.

*Longevity as a cut flower*.—About 1 week.

*Flower aspect*.—Held primarily upright from pedicel.

*Peduncle*.—Strong, robust, somewhat flattened, held erect, average of 45 cm in length and 1 cm in width at distal region and 10 mm in width at proximal region, surface is glabrous, color Yellow-Green 144B.

*Pedicels*.—Strong, average of 3 cm in length and 1 mm in width, held erect to outward, color Green 141C, surface is glabrous.

*Flower buds*.—Obovate in shape, average of 1.5 cm in length and 5 mm in width, color Violet Blue 89C.

*Tepals*.—6, narrow obovate in shape, entire margin, glabrous texture, acute apex, average of 3 cm in length and 9 mm in width, color when young inner surface; Violet Blue 97B, color when young outer surface; Violet Blue 96C, color mature inner surface; Violet Blue 96D, color mature outer surface; Violet Blue 96B, mid rib on all surfaces Violet Blue 94C.

Reproductive organs:

*Gynoecium*.—1 pistil, average of 3 cm in length, stigma is narrow clavate in shape and Violet Blue 91C in color, style is about 3 cm in length and Violet Blue 91C in color, ovary is Yellow-Green 149D in color.

*Androecium*.—6 stamens, anthers are dorsified, oblong in shape, average of 3 mm in length, and Blue 103A in color, filament is 2 cm in length, pollen is low in quantity and Black 202A in color.

*Fruit/seed*.—Have not been observed.

It is claimed:

1. A new and distinct cultivar of *Agapanthus* plant named 'Blue Bayou' as herein illustrated and described.

* * * * *